(12) United States Patent
El-Ghannam

(10) Patent No.: US 8,168,208 B1
(45) Date of Patent: *May 1, 2012

(54) SILICA-CALCIUM PHOSPHATE BIOACTIVE COMPOSITE FOR IMPROVED SYNTHETIC GRAFT RESORBABILITY AND TISSUE REGENERATION

(76) Inventor: Ahmed El-Ghannam, Lexington, KY (US)

( * ) Notice: Subject to any disclaimer, the term of this patent is extended or adjusted under 35 U.S.C. 154(b) by 1186 days.

This patent is subject to a terminal disclaimer.

(21) Appl. No.: 11/267,970

(22) Filed: Nov. 7, 2005

Related U.S. Application Data

(60) Division of application No. 10/741,646, filed on Dec. 19, 2003, now abandoned, which is a continuation-in-part of application No. 10/453,002, filed on Jun. 3, 2003, now abandoned.

(60) Provisional application No. 60/385,082, filed on Jun. 3, 2002.

(51) Int. Cl.
*A61K 9/00* (2006.01)
*A01N 59/00* (2006.01)
*A01N 59/26* (2006.01)
*A01N 59/06* (2006.01)

(52) U.S. Cl. ......... 424/400; 424/600; 424/601; 424/662

(58) Field of Classification Search ......................... None
See application file for complete search history.

(56) References Cited

U.S. PATENT DOCUMENTS

| | | | | |
|---|---|---|---|---|
| 4,828,495 | A * | 5/1989 | Bell et al. | 433/200.1 |
| 5,082,808 | A | 1/1992 | Nonami et al. | |
| 5,262,166 | A * | 11/1993 | Liu et al. | 424/423 |
| 5,643,789 | A * | 7/1997 | Ducheyne et al. | 435/402 |
| 5,762,950 | A * | 6/1998 | Yli-Urpo et al. | 424/422 |
| 5,891,233 | A * | 4/1999 | Salonen et al. | 106/35 |
| 6,224,913 | B1 * | 5/2001 | Ducheyne et al. | 424/602 |

FOREIGN PATENT DOCUMENTS

WO WO 9107357 A1 * 5/1991

OTHER PUBLICATIONS

Langstaff, S. et al., Resorbable Synthetic Bone Grafts Formed from a silicon Stabilized Calcium Phosphate Bioceramic, Mat. Res. Soc Symp Proc. vol. 550, 1999, 313-318.*
Ahmed, Karima, et al., Correlation Between Crystalline Structure and Protein Adsorption onto New Silica-Cotnaining Calcium Phosphate Composites, Society for Biomaterials, $27^{th}$ Annual Metting Transactions, 2001, p. 145.*
The Univeral Compound, TimeDomain CVD, pp. 1-5, Dec. 7, 2000.*
Knabe et al., "Morphological evaluation of osteoblasts cultured on different calcium phosphate ceramics", Biomaterials, 1997, pp. 1339-1347, vol. 18, Elssevier Science Limited, Great Britain.

* cited by examiner

*Primary Examiner* — Scott Long
*Assistant Examiner* — Lyndsey Beckhardt
(74) *Attorney, Agent, or Firm* — Hammer & Associates, P.C.

(57) ABSTRACT

A method is disclosed for the generation of bone tissue by the preparation and the application to bone defect sites of a resorbable silica-calcium phosphate bioactive composite (SCPC) that finds utility as a bone tissue engineering scaffold. The resorbable silica-calcium phosphate bioactive composite can be applied directly to bone defect or can be employed as a bioactive coating on implants to facilitate bone growth around the implant. The resorbable silica-calcium phosphate bioactive composite is prepared from a mixture of a silica salt in an amount to provide between about 0.31 moles and about 0.93 moles of silica and calcium phosphate, said silica salt being present in the resorbable silica-calcium phosphate bioactive composite. The mixture is thermally treated at a temperature ranging between about 130° C. to about 1200° C. to form said resorbable silica-calcium phosphate bioactive composite having a phase composition comprising a thermally treated form of silica and calcium phosphate.

22 Claims, 1 Drawing Sheet

SILICA-CALCIUM PHOSPHATE BIOACTIVE COMPOSITE FOR IMPROVED SYNTHETIC GRAFT RESORBABILITY AND TISSUE REGENERATION

This application is a division of application Ser. No. 10/741,646, filed Dec. 19, 2003, now abandoned which is a continuation-in-part of application Ser. No. 10/453,002, filed Jun. 3, 2003 now abandoned claiming the benefit of the filing date of provisional application Ser. No. 60/385,082, filed Jun. 3, 2002 entitled SILICA-CALCIUM PHOSPHATE COMPOSITE FOR IMPROVED SYNTHETIC GRAFTED RESORBABILITY AND TISSUE REGENERATION, which are incorporated by reference herein.

FIELD OF THE INVENTION

This invention relates to bone tissue generation and more particularly to a method for bone tissue generation employing a method for the generation of bone tissue by the preparation and the application to bone defect sites of a resorbable silica-calcium phosphate bioactive composite (SCPC) that finds utility as a bone tissue engineering scaffold.

BACKGROUND OF THE INVENTION

Silica-based bioactive glasses and calcium phosphate ceramics have long been known to serve as synthetic materials useful in the promotion of bone formation in repairing bone fractures and the like. These materials are considered bioactive because they bond to bone and enhance bone tissue formation with a variable degree of success.

An estimated 11 million people in the United States have at least one medical device implant. Two types of implants, fixation devices (usually fracture fixation) and artificial joints are used in orthopedic treatments and oral and maxillofacial procedures. Approximately 80% of the fracture fixation requires adjuvant grafting. Among the joint replacement procedures an increasing number are revision surgeries with their adjuvant need for bone grafting.

Current approaches to difficult bone repair problems include utilization of autografts, allografts and synthetic grafts. Although at present auto graft material is preferentially used, there is limitation in its use, including donor site morbidity, limited donor bone supply, anatomical and structural problems and elevated levels of resorption during healing. The use of allografts has a disadvantage of eliciting an immunalogical response due to genetic differences and the risk of reducing transmissible diseases. Considerable attention has been directed to the use of synthetic materials for bone graft, most notably hydroxyapatite, tricalcium phosphate and bioactive glass. The synthetic graft material is also used to form coatings on implants, such as pins and the like, to promote attachment of new bone growth to the implement. In addition, these materials are also used as fillers in biopolymer composites and drug delivery vehicles.

SUMMARY OF THE INVENTION

In accordance with the present invention, there is provided a method for the generation of bone tissue by the preparation and the application to bone defect sites of a resorbable silica-calcium phosphate bioactive composite (SCPC) that finds utility as a bone tissue engineering scaffold. The resorbable silica-calcium phosphate bioactive composite can be applied directly to bone defect or can be employed as a bioactive coating on implants to facilitate bone growth around the implant.

The improved SCPC defines a surface that can contain four different phases; 1) silica modified with calcium and/or phosphorous, 2) unmodified silica/silanol groups required to nucleate calcium phosphate precipitation, 3) calcium phosphate modified with silica and 4) unmodified calcium phosphate. These four different phases ensure the availability of a surface with superior bioactivity as compared to calcium phosphate ceramic or bioactive glass conventionally used as a scaffold to promote bone tissue growth. In addition the presence of sodium in the form of $\beta$-$NaCaPO_4$ has a synergistic effect on the absorbability of protein that contributes to improved bioactivity.

While the resorption and bioactivity of bioactive glass is limited by the diffusion of Ca and P ions from the glass bulk to the surface, the resorption and bioactivity of the SCPC does not depend on the bulk composition. In addition to providing an immediate bioactive surface layer that enhances protein adsorption and cell function, the silicon released from the surface may have a stimulatory effect on bone cell function.

The bioactivity and the resorbability of the SCPC is affected and controlled by its chemical composition, which prior to thermal treatment, comprises a mixture of an organic or inorganic silica salt and a calcium phosphate. In addition, its crystalline structure, the degree of the alkaline environment presented by the SCPC composition, its porosity and its thermal treatment temperature combine to provide the improved bioactivity as compared to conventionally used compositions such as bioglass. For example disruption of the crystalline structure of the bioactive phases caused by the exchange of silica in the calcium phosphate phase and the exchange of phosphate into the silica phase improves the bioactivity of the SCPC. Moreover, the corrosion rate and resorbability are enhanced by this ion exchange in the bioactive phases. Similarly the porosity of the SCPC, which may range between about 10 vol % to about 80 vol %, controlled during its formation by particle size of the ingredients, the presence of a fugitive agent or a foaming agent, and/or the pressure applied when forming green shapes prior to sintering, improves bioactivity with increasing porosity. It is preferred that the size of the pores be less than 800 µm and it has been found that good results are achieved when pore size ranges from about 0.1 µm to 500 µm The presence of an alkaline environment, such as provided by the presence of sodium ions, has been found to increase the bioactivity of the SCPC. Likewise the sintering temperature effects a change in the bioactivity and resorbability of the SCPC.

In the present invention after thermal treatment the silica is present both in amorphous form and in crystalline form. The crystal form can comprise L-quartz and/or $\alpha$-cristobalite (tetragonal crystal structure). The silica may be present in amounts ranging from 0.3094 moles to 0.9283 moles. The calcium phosphate portion of the SCPC can be present in many forms such as for example, hydroxyapatite, tricalcium phosphate, dibasic calcium phosphate, calcium pyrophosphate ($\beta$-$Ca_2P_2O_7$ (H)) and/or $\beta$-$NaCaPO_4$ (rhenanite). The precise structure of the SCPC will depend on the initial chemical concentration of each component and on the thermal treatment protocol.

DESCRIPTION OF THE INVENTION

Figure 1:
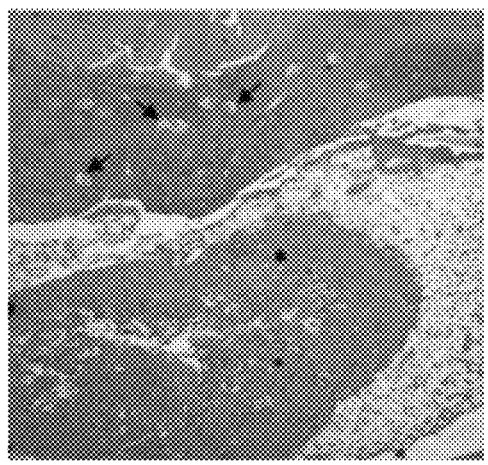
FIGS. 1, 2 and 3 show the results of histological evaluations of critical size bone defects, created in the cortical bone of the femora of New Zealand rabbits.

The SCPC is prepared by forming an aqueous or non-aqueous paste of a sufficient amount of an organic or inorganic silica salt such as sodium silicate to provide between about 0.31 mole and about 0.93 mole of silica in the thermally treated composite and calcium phosphate such as bicalcium phosphate. In the alternative, an alkali metal oxide such as sodium oxide may be included in a mixture comprising silica in place of the sodium silicate. The paste may be pressed into pellets for more convenient handling. It will be understood that the silicate salt and calcium phosphate may be mixed as a dry powder with good results. The mixture, be it in the form of pellets or other formed shape or as a dried powder, is sintered at temperatures ranging from about 130° C. to about 1200° C.

The composition of the samples after thermal treatment, shown in Table 1 below, was determined by X-ray diffraction analysis and scanning electron microscopy. The relatively high molar concentration of silica that derived from a silica salt causes a shift in the 2θ in the position of the characteristic signals of the silica and calcium phosphate phases and is indicative of the silicate-phosphate ion substitution. The ion substitution exchange resulted in significant decrease in the crystallization temperature in both the silica and calcium phosphate phases. For example as shown in the table, cristobalite, which normally is formed when low quartz is heated to around 720° C., was formed in the phase composition of the composite at the lower temperature of 690° C. The formation of these crystalline phases at lower temperature increased the bioactivity of the SCPC.

TABLE 1

| Sample Id. No. | SiO$_2$ (Mole) | Temp (° C.) | Phase Composition |
|---|---|---|---|
| C3S1 | 0.3094 | 355 | L-quartz (L) + β-Ca$_2$ P$_2$O$_7$ (H) + β-Ca$_3$(PO$_4$)$_2$(I) + β-NaCaPO$_4$ (L) |
| C1S1 | 0.6193 | 355 | L-quartz (L) + γ-Ca$_2$ P$_2$O$_7$ (H) + β-Ca$_3$(PO$_4$)$_2$(I) + β-NaCaPO$_4$ (L) |
| C1S3 | 0.9283 | 355 | L-Quartz(L) + β-NaCaPO$_4$ (L) |
| C3S1 | 0.3094 | 690 | a-cristobalite(I) ++ β-Ca$_2$ P$_2$O$_7$ (H) + β-NaCaPO$_4$ (L) |
| C1S1 | 0.6193 | 690 | a-cristobalite (H) + β-NaCaPO$_4$ (H) + L-Quartz |
| C1S3 | 0.9283 | 690 | a-cristobalite (H) + β-NaCaPO$_4$ (H) + Na$_2$Si$_3$O$_5$ |
| C3S1 | 0.3094 | 800 | a-cristobalite (H) ++ β-Ca$_2$ P$_2$O$_7$ (H) + β-NaCaPO$_4$ (H) |
| C1S1 | 0.6193 | 800 | a-cristobalite (H) + β-NaCaPO$_4$ (H) + L-quartz(L) |
| C1S3 | 0.9283 | 800 | a-cristobalite (H) + β-NaCaPO$_4$ (H) + L-quartz(L) |

Following thermal treatment, the SCPC material is ready for use such as by forming granules into a desired shape, such as a block, sphere or sheet or application of a layer of the composite over at least a portion of a suitable prosthesis for implant. For example, the composite can be deposited as a layer on a device such as a pin for insertion in the bone being repaired. In addition the composite may be applied directly to bone being repaired.

As mentioned above, it is highly preferred that the bioactive composite be porous. Good results can be achieved when porosity ranges from 10 vol % to about 80 vol %. For the higher porosities it is preferred to include a suitable pore former such as a fugitive material that is consumed during the thermal treatment process. Likewise, pore formation can be initiated in the raw composite mix by including a foaming agent or a fugitive solvent. Pore forming and fugitive agents for use in ceramic composites are well known and are commercially available and the selection of a suitable agent is clearly understood. In many cases the solvent of the composite paste will itself form pores in sufficient number and size as it leaves the paste during thermal treatment. It is preferred that the pores be less than 800 μm to aid in maintaining the structural integrity of the finished composite. The bioactive composite may have a pore size of between about 0.1 μm to about 500 μm and good results are achieved with pore sizes ranging from about 10 μm to about 300 μm The composites of Table 1 were tested for adsorption of serum protein, a necessary first step to the production of new bone growth around the SCPC, and it was found that protein adsorption varied with the sintering temperature which the material was pretreated at during processing. It was found that protein adsorption dropped as the sintering temperature was increased to about 690° C. and thereafter sharply increased between 690° C. and 800° C. Although it is not fully understood, this may be attributed to the transformation of silica from amorphous phase to a crystalline phase which may inhibit protein adsorption onto the surface of the SCPC thermally treated at the lower temperature below 690° C. However, the silica is transformed from L-quartz into α-cristobalite (after thermal treatment above 690° C.) which is associated with a significant increase in serum protein adsorption. In addition, the formation of β-NaCaPO$_4$ which also begins forming at about 690° C. and increases as the treatment temperature increases above about 690° C. is also associated with a significant increase in serum protein adsorption. Regardless of the thermal treatment, however, the SCPC of the present invention absorbs more protein than the standard bioactive glass alone. Also, the disruption of the structure of the SCPC caused by the exchange of silica in the calcium phosphate phase and the exchange of phosphate into the silica phase improves protein adsorption.

SCPCs, identified in Table 1 as C3S1, C1S1 and C1S3 were sintered at temperatures ranging between 355° C. and 800° C. The phase compositions at several sintering temperatures have been determined and are set out in Table 1.

The compositions were tested for protein absorption as reported by Ahmed, El-Ghannam and Fouda, biomaterials Forum, 27th Annual Meeting Transactions, 23, May-Jun. 2001 in the following manner.

Particles (90-250 μm) from each of the samples were separately immersed in a simulated body fluid comprising fetal bovine serum for 3 hours at 37° C. After immersion the protein was extracted using 1% SDS. Protein concentration was determined using a gold staining dot block technique. For a comparison, a control experiment using bioactive glass particles of the same particle size range was run in parallel. After the samples were cooled down to room temperature they were immersed in protein solution. The adsorbed protein was determined as described above. Samples containing α-cristobalite and β-NaCaPO$_4$ adsorbed statistically significant higher amounts of serum protein than samples containing L-quartz and pyrophosphate. As the amount of the cristobalite increased the adsorption of protein increased.

EXAMPLE 1

The following example illustrates the effect on bone tissue regeneration by the resorbable bioactive SCPC of the present invention.

Samples prepared as described above and identified in Table 1 above as C1S1 and C1S3 and thermally treated at 690° C. were analyzed along with a control consisting of a commercially available bioglass were evaluated for bone tissue response in the following manner.

A rabbit femur model was used to evaluate bone tissue response to the new material. Nine (9) rabbits 3-4 months weighing about 3 kg were used. A critical size bone defect (7 mm in diameter) was created in the cortical bone of each femur. Granules of C1S3 and C1S1 as well as the control bioglass were used separately in sufficient amount to fill the defects. The animals were sacrificed after 3 weeks. Bone segments containing the defects were fixed, dehydrated, decalcified, sliced into thin sections (5-7 micron) and stained with H & E.

Scanning electron microscopic analysis of the C1S3 particles showed a pore size ranging from 10-300 μm. Measurements of porosity using mercury intrusion method showed that the particles acquired 54% porosity. The pore size is large enough to allow for bone cell colonization and vascularization of the newly formed bone. The high porosity percent provides high surface area for bone cell attachment and stimulation of bone bioactivity reactions that results in bone formation. Moreover, the porosity regulates graft material resorption during new bone tissue formation.

Figure 2:
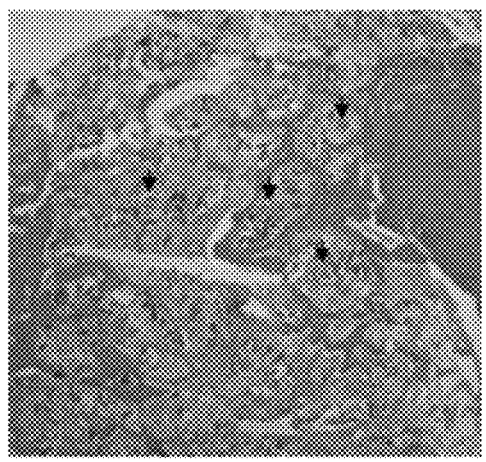
Figure 3:
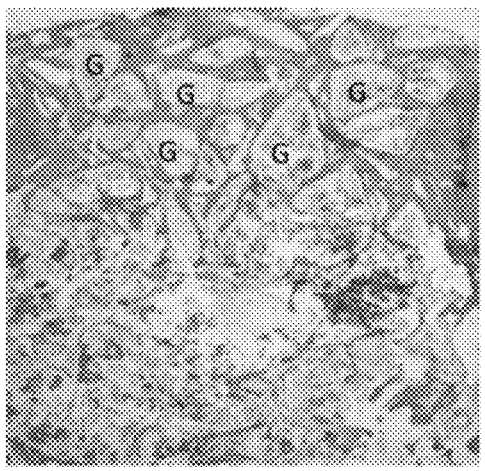

FIGS. 1, 2 and 3 show the histological evaluations of critical size bone defects, created in the cortical bone of the femora of New Zealand rabbits that were grafted with particles (150-600 μm) of C1S3 (FIG. 1), C1S1 (FIG. 2), both sintered at 690° C., and bioactive glass (FIG. 3), the compositions of which are shown in Table 1 above. After 3 weeks, defects grafted with C1S3 were almost completely filled with new bone (FIG. 1). Bone formed in the internal side of the defect has been completely remodeled and few vascular cavities remained. The bone defect treated with composition C1S1 (FIG. 2) also showed substantial development of new bone tissue. The defect treated with bioactive glass (BG) alone (FIG. 3) exhibited less new bone tissue and a considerable amount of BG is observed filling the marrow cavity and the defect itself.

These results indicate that SCPCs containing a high silica concentration not only have strong stimulatory effects on bone cell function but also resorb in harmony with the new bone tissue formation. New bone is also present within the marrow cavity that was initially filled with graft material. The architecture of the remodeled cortical bone and marrow resembles that of normal healthy bone. This indicates that the composition of the present invention, particularly the C1S3 material, has a strong stimulatory effect on stem cell differentiation into osteoblasts and can be used as a delivery system for mesnechymal stem cells. EDX analysis of the new bone that formed inside the defect indicates that it is mineralized bone with a Ca/P ratio of 1.65. On the other hand, defects grafted with BG were filled with a substantial quantity of graft materials in addition to bone. It is interesting to note that new bone tissue formed not only on the outer surfaces of C1S1 particles but also inside the pores of the particulates. These results clearly demonstrate that the porous SCPC of the present invention is highly bioactive in that it has a strong stimulatory effect on bone cell attachment, proliferation, differentiation and bone tissue regeneration.

The foregoing example is by way illustration only and should not be taken as limiting the invention. Although preferred embodiments have been described herein in detail, it is understood by those skilled in the art that variations may be made thereto without departing from the spirit and scope of the invention as defined by the claims appended hereto.

Having described the invention I claim:

1. A method for the stimulation of bone tissue growth by application of a resorbable silica-calcium phosphate bioactive composite comprising the steps of:
   a. preparing a mixture comprising:
      a silica salt, said silica salt being sodium silicate;
      a calcium phosphate, said calcium phosphate being bicalcium phosphate $CaHPO_4 \cdot H_2O$; and
      a pore former, said pore former being selected from the group comprising:
   a foaming agent, a fugitive solvent, or a combination thereof;
      said silica salt being present in an amount to provide between about 0.31 mole and about 0.93 mole of silica, wherein the molar concentration of silica that derived from said silica salt is indicative of the silicate-ion substitution in the resorbable silica-calcium phosphate bioactive composite,
   b. subjecting said mixture in the system sodium silicate-calcium phosphate to thermal treatment at a temperature ranging between 355° C. to 800° C. to form said resorbable silica-calcium phosphate bioactive composite having a phase composition comprising a thermally treated porous form of silica and calcium phosphate with pores that are 800 μm or less in size and wherein said silica is in both amorphous and crystalline forms;
   c. applying said resorbable silica-calcium phosphate bioactive composite in a suitable form to an area of bone defect to stimulate the formation and growth of bone tissue.

2. The method of claim 1 wherein said mixture includes an effective amount of sodium oxide.

3. The method of claim 1 wherein said resorbable silica-calcium phosphate bioactive composite is applied directly to a bone defect for the regeneration of bone tissue thereat.

4. The method of claim 1 wherein said resorbable silica-calcium phosphate bioactive composite is applied as a layer over the surface of an implant thereby to stimulate bone tissue regeneration when said implant is inserted into a bone.

5. The method of claim 1 wherein said resorbable silica-calcium phosphate bioactive composite is formed into a shape for implant of said shape.

6. The method of claim 1 wherein said mixture comprises sodium silicate in an amount equivalent to 0.3094 mole silica, said mixture being thermally treated at a temperature of 355° C. to define a phase composition comprising L-quartz (L)+ $\beta$-$Ca_2P_2O_7$(H)+$\beta$-$Ca_3(PO_4)_2$+$NaCaPO_4$.

7. The method of claim 1 wherein said mixture comprises sodium silicate in an amount equivalent to 0.6193 mole silica, said mixture being thermally treated at a temperature of 355° C. to define a phase composition comprising L-quartz+$\gamma$-$Ca_2P_2O_7$+$\beta$-$Ca_3(PO_4)_2$+$\beta$-$NaCaPO_4$.

8. The method of claim 1 wherein said mixture comprises sodium silicate in an amount equivalent to 0.9283 mole silica, said mixture being thermally treated at a temperature of 355° C. to define a phase composition comprising L-quartz+$\beta$-$NaCaPO_4$.

9. The method of claim 1 wherein said mixture comprises sodium silicate in an amount equivalent to 0.3094 mole silica, said mixture being thermally treated at a temperature of 690° C. to define a phase composition comprising $\alpha$-cristobalite$^+$+ $\beta$-$Ca_2P_2O_7$+$\beta$-$NaCaPO_4$.

10. The method of claim 1 wherein said mixture comprises sodium silicate in an amount equivalent to 0.6193 mole silica, said mixture being thermally treated at a temperature of 690° C. to define a phase composition comprising $\alpha$-cristobalite$^+$+ $\beta$-$Ca_2P_2O_7$+$\beta$-$NaCaPO_4$+L-Quartz.

11. The method of claim 1 wherein said mixture comprises sodium silicate in an amount equivalent to 0.9283 mole silica, said mixture being thermally treated at a temperature of 690° C. to define a phase composition comprising α-cristobalite$^+$+β-NaCaPO$_4$+Na$_2$Si$_3$O$_5$.

12. The method of claim 1 wherein said mixture comprises sodium silicate in an amount equivalent to 0.3094 mole silica, said mixture being thermally treated at a temperature of 800° C. to define a phase composition comprising α-cristobalite$^+$+β-Ca$_2$P$_2$O$_7$+β-NaCaPO$_4$.

13. The method of claim 1 wherein said mixture comprises sodium silicate in an amount equivalent to 0.6193 mole silica, said mixture being thermally treated at a temperature of 800° C. to define a phase composition comprising α-cristobalite$^+$+β-NaCaPO$_4$+L-Quartz.

14. The method of claim 1 wherein said mixture comprises sodium silicate in an amount equivalent to 0.9283 mole silica, said mixture being thermally treated at a temperature of 800° C. to define a phase composition comprising α-cristobalite$^+$ (in solid solution (SS))+β-NaCaPO$_4$ (SS)+L-Quartz (SS)+amorphous phase.

15. The method of claim 1 wherein said crystalline form is selected from the group consisting of L-Quartz and α-cristobalite.

16. The method of claim 1 wherein said resorbable silica-calcium phosphate bioactive composite include calcium phosphate in both the amorphous and crystalline forms.

17. The method of claim 16 wherein said crystalline form is selected from the group consisting of hydroxyapatite, tricalcium phosphate, dibasic calcium phosphate, calcium pyrophosphate (β-Ca$_2$P$_2$O$_7$).

18. The method of claim 1 wherein said resorbable silica-calcium phosphate bioactive composite has a porosity of between about 10 volume percent to about 80 volume percent.

19. The method of claim 1 wherein said thermally treated forms of silica and calcium phosphate have reduced crystallization temperatures resulting in improved bioactivity for said resorbable silica-calcium phosphate bioactive composite.

20. The method of claim 1 wherein said resorbable silica-calcium phosphate bioactive composite having pores in the range of 0.01 μm and 500 μm.

21. The method of claim 1 wherein the crystalline phases in said resorbable silica-calcium phosphate bioactive composite are in the form of solid solutions.

22. The method of claim 1 wherein said resorbable silica calcium phosphate bioactive composite contains crystalline and amorphous phases.

\* \* \* \* \*